(12) United States Patent
McKay, Jr.

(10) Patent No.: US 6,319,478 B1
(45) Date of Patent: Nov. 20, 2001

(54) AIR FRESHENER AND INSECT REPELLANT

(75) Inventor: Nicholas D. McKay, Jr., Alpharetta, GA (US)

(73) Assignee: Helmac Products Corporation, Alpharetta, GA (US)

(*) Notice: Subject to any disclaimer, the term of this patent is extended or adjusted under 35 U.S.C. 154(b) by 0 days.

(21) Appl. No.: 09/767,814

(22) Filed: Jan. 23, 2001

(51) Int. Cl.[7] ........................................ A62B 7/08
(52) U.S. Cl. ........................ 422/124; 424/412; 51/181 R
(58) Field of Search ............................... 422/122; 239/54, 239/55, 57; 451/28; 424/412; 51/181 R

(56) References Cited

U.S. PATENT DOCUMENTS 4,918,871 * 4/1990 Widmann ........................ 51/181 R
5,098,713 * 3/1992 Mattesky ........................ 424/412

* cited by examiner

Primary Examiner—Robert J. Warden, Sr.
Assistant Examiner—Sean Conley
(74) Attorney, Agent, or Firm—Gifford, Krass, Groh, Sprinkle, Anderson & Citkowski, P.C.

(57) ABSTRACT

An air freshener and insect repellant having a housing with a wall section. An abrasive strip is secured to the wall section of the housing while a cedar block is movably mounted to the housing so that, upon movement of the cedar block relative to the housing, the abrasive strip abrades an outer surface of the cedar block. A resilient pad is also sandwiched in between the housing wall section and the abrasive strip.

9 Claims, 2 Drawing Sheets

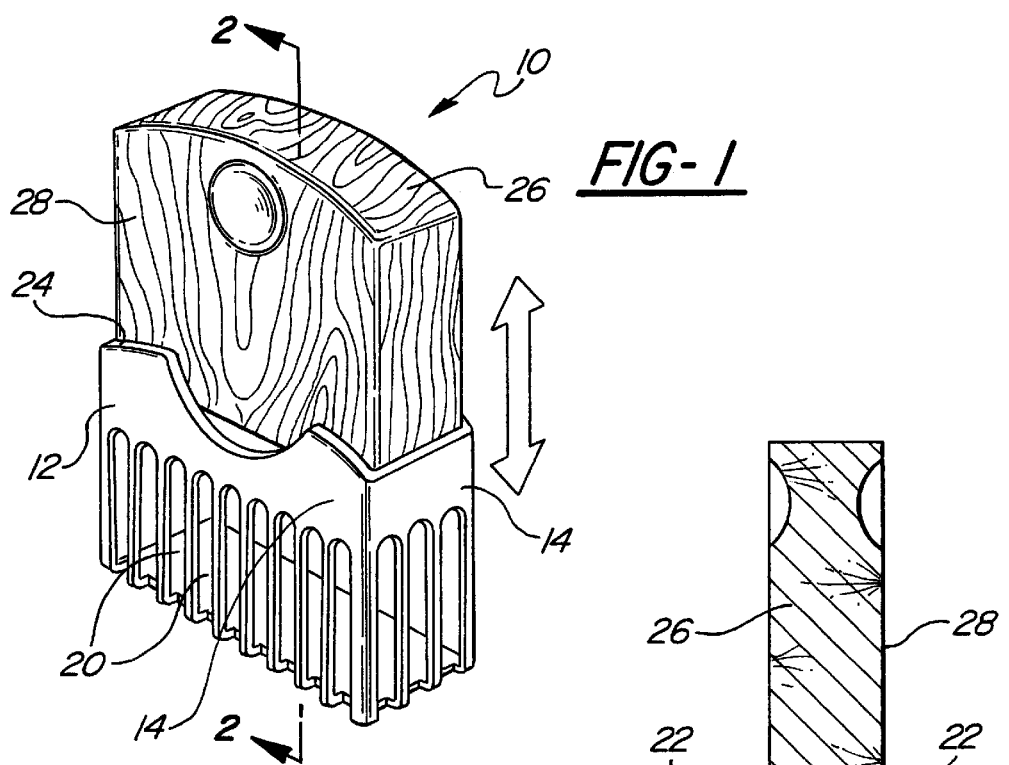
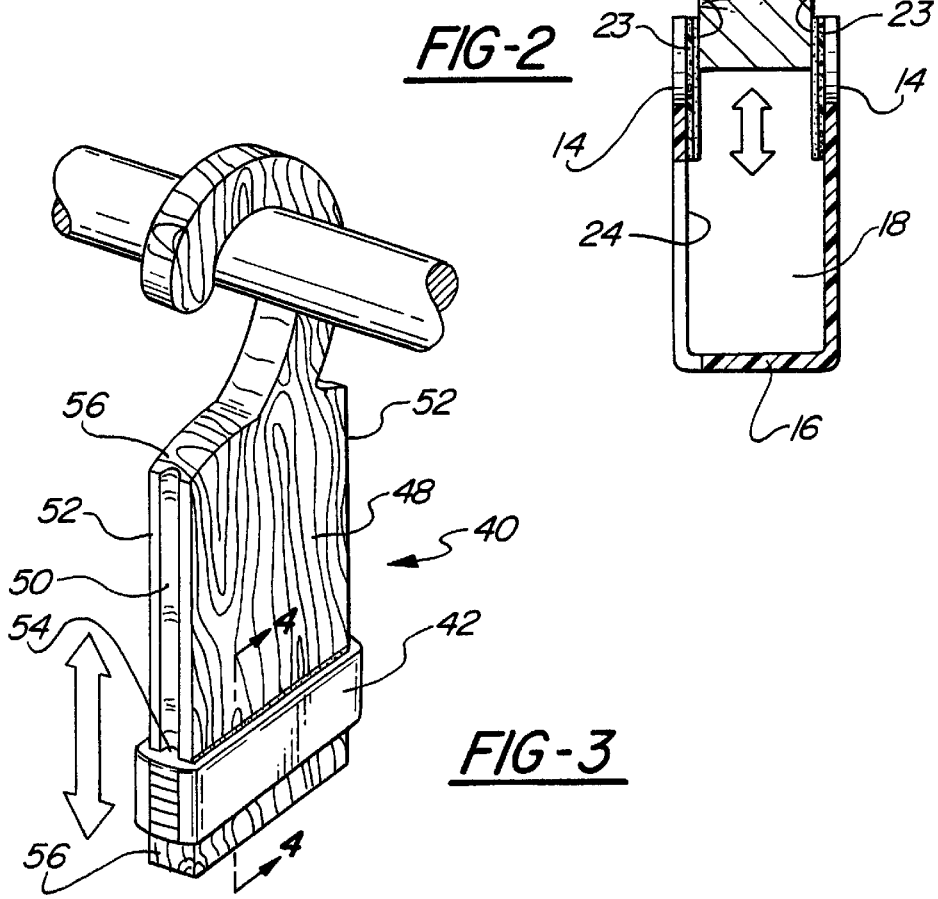

AIR FRESHENER AND INSECT REPELLANT

BACKGROUND OF THE INVENTION

I. Field of the Invention

The present invention relates generally to cedar products utilized as air fresheners and insect repellants.

II. Description of Related Art

Cedar products have long been used both as air fresheners as well as insect repellants. Most notably, the aroma from cedar products is known to repel certain types of insects, such as moths.

These previously known cedar products have come in a number of different sizes, shapes and configurations. For example, in one type of previously known cedar product, cedar blocks or cedar balls are placed in clothes closets or clothes drawers which may be subject to insect infestation.

One disadvantage of the previously known cedar products which are used as air fresheners and insect repellants is that such cedar products emit the cedar aroma necessary to freshen the air and repel insects by diffusing the aroma from the surface of the cedar product. After a period of time, however, the diffusion of the aroma from the cedar products dissipates the source of the aroma from the surface of the cedar product thus decreasing the amount of the aroma. When this happens, the amount of aroma emanating from the cedar product is so minor that the cedar product is no longer effective in either freshening the air or repelling insects.

It has been known, however, that the freshness of the cedar scent from the cedar products can be restored by abrading the surface of the cedar product with sandpaper or other abrasives. Such abrasives remove the top layer from the outer surface of the cedar product thus exposing "fresh" cedar and restoring the emission of the cedar aroma from the cedar product.

In practice, however, users of cedar products have found it inconvenient to abrade the outer surface of the cedar product after prolonged use in order to restore the freshness to that cedar product. Instead, many users have simply discarded the old cedar product and replaced it with new cedar product. While effective, this previously known procedure is wasteful and expensive.

SUMMARY OF THE PRESENT INVENTION

The present invention provides an air freshener/insect repellant which overcomes all of the above-mentioned disadvantages of the previously known devices.

In brief, the air freshener/insect repellant of the present invention comprises a housing having a wall section. An abrasive strip, such as a strip of sandpaper, is then secured to at least a portion of that wall portion.

A cedar block is then movably mounted to the housing so that, upon movement of the cedar block relative to the housing, the abrasive strip abrades an outer surface of the cedar block. In doing so, the abrasive strip removes an outer aged layer from the cedar block thus restoring the cedar block to a fresh condition in which the aroma from the cedar block is restored.

There are several different preferred embodiments of the present invention. In one preferred embodiment, the housing is generally rectangular and tubular in shape with the abrasive strip positioned on the inside surface of the housing. The cedar product is then slidably mounted through the interior of the housing and is dimensioned so that, upon movement of the cedar block relative to the housing, the abrasive strip secured to the housing abrades the outer surface of the cedar block.

In still a further embodiment of the present invention, the housing is generally tubular and cylindrical in shape with the abrasive strip secured to at least a portion of the interior surface of the housing. The cedar block, in turn, is cylindrical in shape and disposed within the interior cavity of the housing. Furthermore, the cedar block is dimensioned so that, upon rotation of the cedar block relative to the housing, the abrasive strip secured to the housing abrades and removes the outer surface of the cedar block.

In both cases, the housing preferably includes at least one and preferably several ventilation openings to expose the outer surface of the cedar block to the outside of the housing. Furthermore, a resilient pad is preferably sandwiched in between the abrasive strip and the housing to ensure contact between the abrasive strip and the cedar block.

BRIEF DESCRIPTION OF THE DRAWINGS

A better understanding of the present invention will be had upon reference to the following detailed description, when read in conjunction with the accompanying drawing, wherein like reference characters refer to like parts throughout the several views, and in which:

FIG. 1 is a perspective view illustrating a first preferred embodiment of the present invention;

FIG. 2 is a view taken substantially along line 2—2 in FIG. 1;

FIG. 3 is a view similar to FIG. 1, but illustrating a further embodiment of the present invention;

DETAILED DESCRIPTION OF PREFERRED EMBODIMENTS OF THE PRESENT INVENTION

Figure 4:
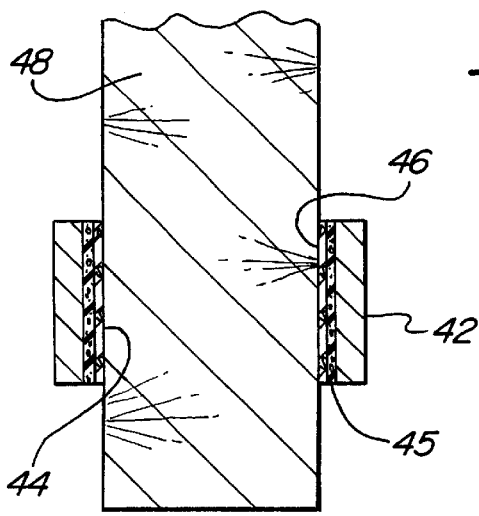
FIG. 4 is a sectional view taken substantially along line 4—4 in FIG. 3.

With reference first to FIGS. 1 and 2, a first preferred embodiment of the air freshener/insect repellant 10 (hereinafter called "insect repellant") of the present invention is illustrated. The insect repellant 10 includes a housing 12 which may be constructed of any conventional rigid material, such as wood, plastic or the like.

The housing 12 includes a plurality of connected sidewall portions 14 and a bottom wall 16. The sidewall sections 14 form a generally rectangular channel within the interior of the wall sections 14. Furthermore, as best shown in FIG. 1, the wall sections 14 include a plurality of ventilation openings 20 for a purpose to be subsequently described.

With reference now particularly to FIG. 2, an abrasive strip 22, such as a sandpaper strip, is secured to the inside surface 24 of at least one, and preferably several wall sections 14. As shown in FIGS. 1 and 2, the abrasive strip 22 is disposed around the interior surface 24 of the wall sections 14 adjacent an end 24 of the housing 12 opposite from the bottom wall 16. Preferably, a resilient pad 23 is sandwiched between the abrasive strip 22 and the housing 12.

Referring again to FIGS. 1 and 2, a cedar block 26 is dimensioned to be slidably received through the open upper end 24 of the housing 12 and into the interior cavity 18 of the housing 12. Furthermore, the cedar block 26 is dimensioned so that, as the block 26 is slidably moved relative to the housing 12, the abrasive strip 22 contacts the outer surface 28 of the block 26 and abrades the outer surface 28 of the block 26. The resilient pad 23 ensures contact between the strip 22 and the cedar block 26. Such abrasion of the outer surface 28 of the block 26 effectively renews the aroma from the cedar block 26 and this aroma emanates either through the ventilation openings 20 of the housing 12 or directly from the portion of the block 26 exposed from the housing 12.

With reference now to FIGS. 3 and 4, a further embodiment of an insect repellant 40 of the present invention is illustrated. As best shown in FIG. 3, the insect repellant 40 includes a tubular housing 42 which is constructed of any rigid material, such as plastic, metal or wood. The housing 42, furthermore, is tubular thus having an interior surface 44 (FIG. 4). Furthermore, as best shown in FIG. 4, an abrasive strip 46 is positioned along the inside surface 44 of the housing 42 and a resilient pad 45 is sandwiched between the abrasive strip 46 and the housing 42.

An elongated and generally rectangular block 48 is slidably disposed through the housing 42. Furthermore, the block 48 is dimensioned so that, as the block 48 moves relative to the housing 42, the abrasive strip 46 on the interior surface 44 of the housing 42 contacts and abrades the outer surface of the cedar block 48. In doing so, the aroma from the cedar block 44 is restored in the desired fashion.

With reference now particularly to FIG. 3, in order to retain the housing 42 to the cedar block 48, the cedar block 48 preferably includes an elongated recess 50 formed along at least one, and preferably two opposed sides 52 of the cedar block 48. The housing 42, in turn, includes a tab 54 which is received within the recess 50. Furthermore, the recess 50 is closed at each of its ends 56 thus entrapping the housing 42 between the closed ends 56 of the recess 50.

Figure 5:
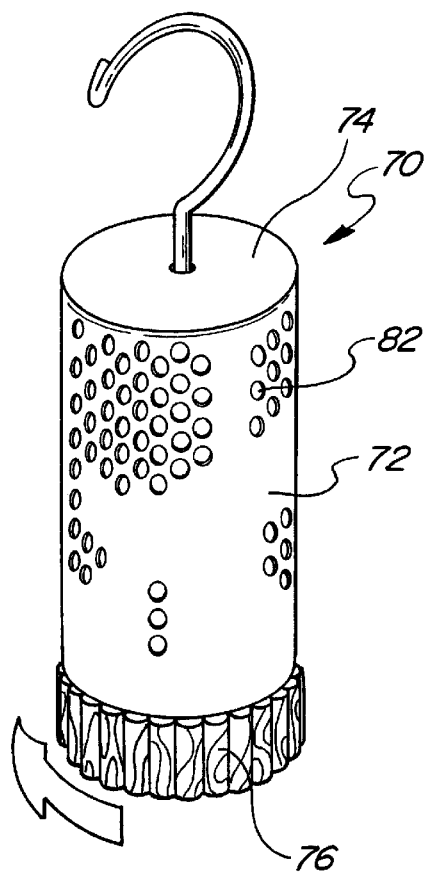
FIG. 5 is an elevational view of still a further preferred embodiment of the present invention.
Figure 6:
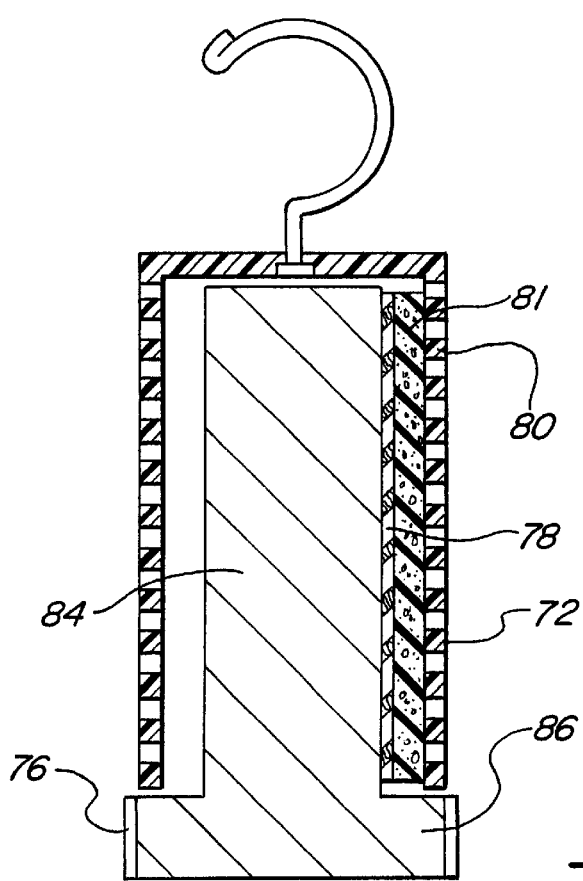
FIG. 6 is a view taken substantially along line 6—6 in FIG. 5.

With reference now to FIGS. 5 and 6, a still further preferred embodiment of the insect repellant 70 of the present invention is illustrated. The insect repellant 70 includes an elongated tubular and cylindrical housing 72 which is closed at one end 74 and open at its other end 76. An abrasive strip 78 is provided along at least a portion of an interior surface 80 of the housing 72 and a resilient pad 81 is sandwiched between the abrasive strip 78 and the housing 72. Additionally, as shown in FIG. 5, the housing 72 preferably includes a plurality of ventilation openings 82.

A tubular and cylindrical cedar block 84 is then positioned within the housing 72. The cedar block 84 is dimensioned so that, upon rotation of the cedar block 84 relative to the housing 72, the abrasive strip 78 contacts the outer surface of the cedar block 84 thus abrading the outer surface of the cedar block 84 and restoring the cedar freshness to the cedar block 84.

In order to facilitate the rotation of the cedar block 84, an enlarged diameter knob 86 is secured to one end of the cedar block 84. This knob 86 abuts against the open end 76 of the housing 72 and may be either separate from the cedar block 84 or integrally formed with the cedar block 84.

From the foregoing, it can be seen that the present invention provides a simple and yet highly effective cedar air freshener/insect repellant. Having described my invention, however, many modifications thereto will become apparent to those skilled in the art to which it pertains without deviation from the spirit of the invention as defined by the scope of the appended claims.

I claim:

1. An air freshener/insect repellant comprising:
   a housing having a wall section,
   a cedar block,
   an abrasive strip secured to said wall section of said housing, and
   said cedar block being movably mounted to said housing so that, upon movement of said cedar block relative to said housing, said abrasive strip abrades an outer surface of said cedar block.

2. The invention as defined in claim 1 wherein said housing further comprises a plurality of wall sections which together form a channel, said cedar block being slidably disposed through said channel.

3. The invention as defined in claim 2 and comprising means for retaining said housing to said cedar block.

4. The invention as defined in claim 3 wherein said retaining means comprises an elongated recess formed along one side of said cedar block, said housing having a tab disposed in said recess.

5. The invention as defined in claim 1 wherein said housing section is generally tubular and cylindrical in shape thus forming a cylindrical chamber, and wherein said cedar block is cylindrical in shape and rotatably mounted in said housing chamber.

6. The invention as defined in claim 1 wherein said housing wall section includes a plurality of ventilation openings.

7. The invention as defined in claim 5 and comprising an enlarged diameter knob at one end of said cedar block.

8. The invention as defined in claim 7 wherein said knob abuts against one end of said housing.

9. The invention as defined in claim 1 and comprising a resilient pad sandwiched between said abrasive strip and said housing wall section.

* * * * *